(12) United States Patent
Wang et al.

(10) Patent No.: US 11,324,457 B2
(45) Date of Patent: May 10, 2022

(54) EXPLAINABLE ARTIFICIAL INTELLIGENCE FRAMEWORK FOR ELECTROCARDIOGRAPHY ANALYSIS

(71) Applicant: TENCENT AMERICA LLC, Palo Alto, CA (US)

(72) Inventors: Kun Wang, San Jose, CA (US); Nan Du, Santa Clara, CA (US); Yusheng Xie, Mountain View, CA (US); Min Tu, Cupertino, CA (US); Shangqing Zhang, San Jose, CA (US); Yaliang Li, Santa Clara, CA (US); Tao Yang, Mountain View, CA (US); Hui Tang, Mountain View, CA (US); Lianyi Han, Palo Alto, CA (US); Wei Fan, New York, NY (US)

(73) Assignee: TENCENT AMERICA LLC, Palo Alto, CA (US)

( * ) Notice: Subject to any disclaimer, the term of this patent is extended or adjusted under 35 U.S.C. 154(b) by 442 days.

(21) Appl. No.: 16/253,942

(22) Filed: Jan. 22, 2019

(65) Prior Publication Data

US 2020/0229771 A1  Jul. 23, 2020

(51) Int. Cl.
```
A61B 5/00      (2006.01)
G06K 9/00      (2022.01)
A61B 5/316     (2021.01)
A61B 5/349     (2021.01)
G06N 20/00     (2019.01)
```
(52) U.S. Cl.
CPC ............ *A61B 5/7275* (2013.01); *A61B 5/316* (2021.01); *A61B 5/349* (2021.01); *A61B 5/7264* (2013.01); *G06K 9/00523* (2013.01); *G06K 9/00536* (2013.01); *G06N 20/00* (2019.01)

(58) Field of Classification Search
CPC ...... A61B 5/349; A61B 5/7264; A61B 5/7275
See application file for complete search history.

(56) References Cited

U.S. PATENT DOCUMENTS

| | | | |
|---|---|---|---|
| 4,589,420 A | 5/1986 | Adams et al. | |
| 2005/0090867 A1 | 4/2005 | Lapanashvili et al. | |
| 2006/0184056 A1 | 8/2006 | de Chazal et al. | |
| 2016/0089047 A1 | 3/2016 | Jonnada et al. | |
| 2019/0059763 A1* | 2/2019 | Shakur | A61B 5/02438 |

FOREIGN PATENT DOCUMENTS

WO   2018/162901 A2   9/2018

OTHER PUBLICATIONS

International Search Report in International Application No. PCT/US2019/035366, dated Aug. 26, 2019.
Written Opinion in International Application No. PCT/US2019/035366, dated Aug. 26, 2019.

* cited by examiner

*Primary Examiner* — Joseph M Dietrich
(74) *Attorney, Agent, or Firm* — Sughrue Mion, PLLC (57) ABSTRACT

There is included an apparatus and system including an intra-heartbeat (HB) extraction code configured to extract intra-HB features from electrocardiography (ECG) signals, and an inter-HB extraction code configured to extract inter-HB features from the ECG signals, and at least one attention mechanism code configured to control at least one of the intra-HB extraction code and inter-HB extraction code based on at least one attention mechanism.

16 Claims, 5 Drawing Sheets

EXPLAINABLE ARTIFICIAL INTELLIGENCE FRAMEWORK FOR ELECTROCARDIOGRAPHY ANALYSIS

BACKGROUND

1. Field

The disclosed subject matter relates to an explainable artificial intelligence framework designed, for example, for electrocardiography (ECG) signal data analysis which can be applied widely in ECG classification, computer-aided diagnosis, bed-side alarms and patient ECG monitoring.

2. Description of Related Art

Related art is incapable of providing a comprehensive ECG diagnosis and analysis system even though ECG exams are among the most common medical procedures to help doctors diagnose many heart diseases, including atrial fibrillation, myocardial infarction, and acute coronary syndrome (ACS).

Annually, around 300 million ECGs are recorded (NPL 1). Conventional approaches for ECG analysis tend to use digital signal processing algorithms, such as wavelet transformations (NPL 2 and 3), to compute features from ECG signals. However, such approaches are not comprehensive, and thus, using those features alone is insufficient to distinguish between multiple types of heart arrhythmias. As such, there has been an attempt to address such technical problem by adoption of deep neural networks, such as convolutional neural networks (CNN) (NPL 4) and recurrent neural networks (RNN) in attempt to achieve good accuracy for multi-class classification task based on ECG signals.

NPL 1: Hedén, B., Ohlsson, M., Holst, H., Mjöman, M., Rittner, R., Pahlm, O., . . . & Edenbrandt, L. (1996). Detection of frequently overlooked electrocardiographic lead reversals using artificial neural networks. *American Journal of Cardiology*, 78(5), 600-604.

NPL 2: Li, C., Zheng, C., & Tai, C. (1995). Detection of ECG characteristic points using wavelet transforms. *IEEE Transactions on biomedical Engineering*, 42(1), 21-28.

NPL 3: Martínez, J. P., Almeida, R., Olmos, S., Rocha, A. P., & Laguna, P. (2004). A wavelet-based ECG delineator: evaluation on standard databases. *IEEE transactions on biomedical engineering*, 51(4), 570-581.

NPL 4: Rajpurkar, P., Hannun, A. Y., Haghpanahi, M., Bourn, C., & Ng, A. Y. (2017). Cardiologist-Level Arrhythmia Detection with Convolutional Neural Networks. *arXiv.org*.

Although existing approaches for cardiologic tasks have attempted promising results in terms of accuracy, there are still several challenges and shortages. For example, such machine learning and deep learning lack provision of an ability for explanation by the doctors, technicians and researchers. For example, the researcher, as well as the cardiologists, cannot directly using the models to explain where and how the model makes some final decision. Further, such systems generally extract intra- and interheartbeat features from two separated dimensions thereby making it technically difficult to extract both easily with existing single models.

In short, models employed by existing approaches break the typical diagnosis procedures which cardiologists use in real world by their lack of provision of ability for explanation by which comprehensive decisions cannot be made due to unmanageable complexity, and a technical solution to these problems is desired by which to achieve multiple data analysis tasks with multiple sets of ECG features.

SUMMARY

There is presently presented an explainable artificial intelligence framework designed for electrocardiography (ECG) signal data analysis and which can be applied widely in ECG classification, computer-aided diagnosis, bed-side alarms and patient ECG monitoring and may locate and pattern how a set of ECG signals are used to diagnosis an abnormal symptoms or a cardiac disease.

That is, there is provided a new artificial intelligence framework for ECG analysis, which accepts ECG signals as inputs and provides possible analysis outcomes as well as the reasons of decision.

According to exemplary embodiments, there is an apparatus and a method in which there is at least one memory, configured to store computer program code, at least one hardware processor, configured to access said computer program code and operate as instructed by said computer program code. Said computer program code including an intra-heartbeat (HB) extraction module code configured to extract intra-HB features from electrocardiography (ECG) signals, an inter-HB extraction module code configured to extract inter-HB features from the ECG signals, and at least one attention mechanism code configured to control at least one of the intra-HB extraction module code and inter-HB extraction module code based on at least one attention mechanism.

According to exemplary embodiments, the apparatus and method further include computer program code that includes extraction module pool code configured to extract at least one extraction model from an extraction module pool and apply the at least one extraction model to extraction of at least one of the intra-HB features and the inter-HB features by a corresponding one of the intra-HB extraction module code and the inter-HB extraction module code.

According to exemplary embodiments, the apparatus and method further include computer program code wherein the intra-HB extraction module code is further configured to extract the intra-HB features in parallel with extraction of the inter-HB features by the inter-HB extraction module code.

According to exemplary embodiments, the apparatus and method further include computer program code that includes a second inter-HB extraction module code configured to extract second inter-HB features from the ECG signals in parallel with both of the extraction of the intra-HB features by the intra-HB extraction module code and the extraction of the inter-HB features by the inter-HB extraction module code.

According to exemplary embodiments, the apparatus and method further include computer program code that includes the at least one attention mechanism code is configured to control the intra-HB extraction module code based on the at least one attention mechanism, and wherein the computer program code further includes a second attention mechanism code configured to control the inter-HB extraction module code based on a second attention mechanism, and a third attention mechanism code configured to control the second inter-HB extraction module code based on a third attention mechanism.

According to exemplary embodiments, the apparatus and method further include computer program code that includes ECG analysis module code configured to obtain and statistically process the intra-HB features and the inter-HB features.

According to exemplary embodiments, the apparatus and method further include computer program code that includes task specific module pool code configured to extract at least one task specific model from a task specific module pool and apply the at least one task specific model to statistically process the intra-HB features and the inter-HB features by the task specific module pool code.

According to exemplary embodiments, the apparatus and method further include the ECG analysis module code that is further configured to output at least one of a classification result, an outlier alarm and a predicted diagnosis based on a result of statistically processing the intra-HB features and the inter-HB features.

According to exemplary embodiments, the apparatus and method further include statistically processing the intra-HB features and the inter-HB features by at least one of batch normalization and instance normalization based on the at least one task specific model.

According to exemplary embodiments, the apparatus and method further include computer program code that includes feedback link code configured to feedback an output of the ECG analysis module code to the at least one attention mechanism, and the at least one attention mechanism code is configured to update the attention mechanism based on the output.

BRIEF DESCRIPTION OF THE DRAWINGS

Further features, nature, and various advantages of the disclosed subject matter will be more apparent from the following detailed description and the accompanying drawings in which.

DETAILED DESCRIPTION

Figure 1:
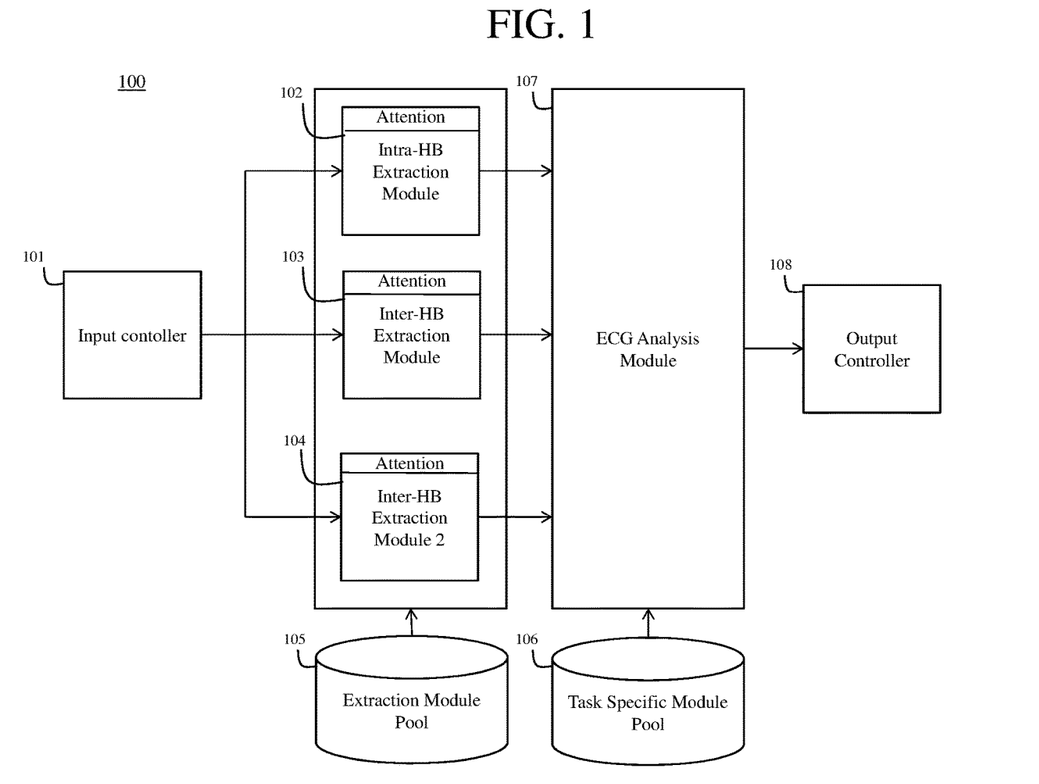
FIG. 1 is a schematic illustration of a simplified block diagram of a system in accordance with an embodiment.

FIG. 1 is an illustration of a simplified block diagram of a system 100 in accordance with an embodiment.

There is an input controller 101 configured to receive ECG signal data, either input from a network or from plural electrodes obtaining heartbeat electrical signals from a body. In attempting to analyze a heartbeat (HB) and make some diagnosis, two levels or types of signal patterns may be considered. First types of signal patterns are intra-heartbeat patterns which capture signal changes with single heartbeats, and second types of signal patterns are inter-heartbeat patterns by which measurements of shape alternations among all heartbeats may be obtained.

A standard ECG report contains signals from a number of different leads, such as 12 different leads, which require a number of electrodes, such as 10 electrodes, in contact with the body. These electrodes are located on different specific locations of body. With such geometric placements, ECG can measure and trace electrophysiological patterns during each heartbeat. Further, the electrical changes collected from electrodes are used to derive waveform signals on multiple axes.

When diagnosing with ECG signal, two levels of signal patterns will cardiologists and doctors consider: one is intra-heartbeat pattern which captures the signal changes with single heartbeats; the other is inter-heartbeat pattern which measures shape alternations among all heartbeat. The input controller 101 may receive such signal patterns and provide those patterns to various modules.

There are provided various feature extraction modules, such as intra-HB extraction module 102, and one or more inter-HB extraction modules 103 and 104, by which input ECG signal data may be analyzed and high-level data features may be extracted.

Machine learning attention mechanisms are attached to each extraction modules 102, 103 and 104 as illustrated in FIG. 1, and serve to focus the extraction modules. For example, the focus may be to track certain features of the ECG signal data in greater resolution while also tracking similar features in lower resolution, and such tracking may be adjust that focus over time and based on use of one or more models, from the pool 105, and results of analyzing the ECG signal data.

Further, the ECG analysis module 107 may result results of extraction and attention based analysis from the extraction modules 102, 103 and 104, and the ECG analysis module 107 will finish specific tasks with such results by drawing one or more models from the task specific module pool 106 and by performing clustering, classification, prediction, etc., and then achieve the final goal of the framework. For example, ECG classification, computer-aided diagnosis, bed-side alarms and patient ECG monitoring may be output to a display or to a network to alert a user, such as a doctor, technician or researcher.

The task specific module pool 106 is a collection of different models served for various ECG related tasks. For instance, several statistical process control algorithms for ECG monitoring and alarming, several predictive models and classifier models for computer-aided diagnosis, and some statistical tools for general pathological status calculation. Depending on the goal of using the framework, the ECG analysis module 107 will deploy one or more appropriate tools from the task specific module pool 106 to finish an end-to-end framework and achieve the final goal.

Figure 2:
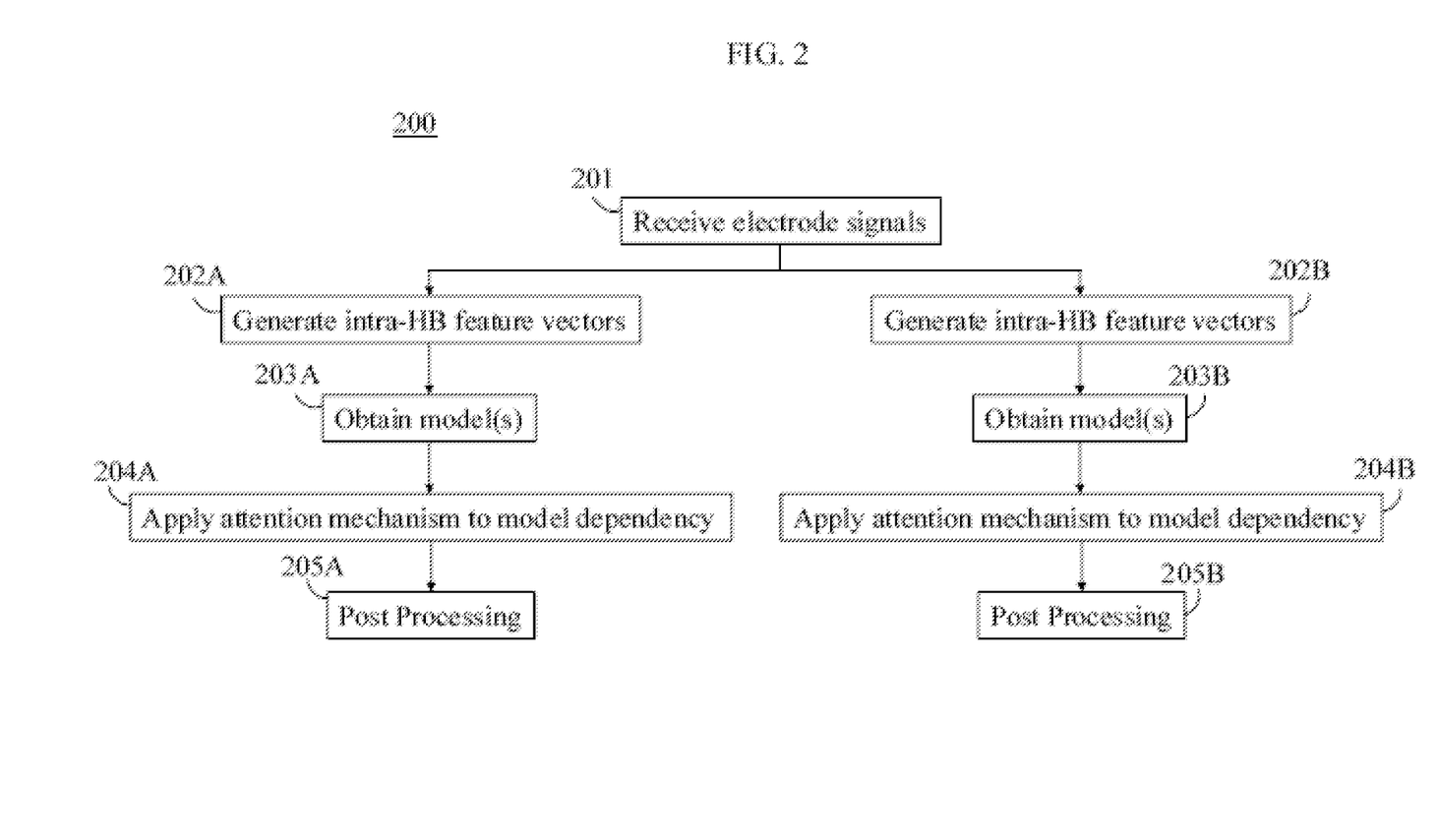
FIG. 2 is a schematic illustration of a simplified flow chart of a communication system in accordance with an embodiment.

FIG. 2 illustrates a flowchart 200 regarding obtaining the ECG signal data at element 101 and analyzing those ECG signal data at the extraction modules 102, 103 and 104 with their attention based learning and models from the extraction module pool 105.

At S201, ECG signal data is received and distributed to ones of the extraction modules 102, 103 and 104.

At S202A, the extraction module 102 accepts pre-processed data as inputs, and generates intra-HB feature vectors as outputs.

Model-wise, at S203A, the extraction module 102 receives one or more models from the extraction module pool 105, and such models include conventional machine learning approaches such as support vector machine (SVM), random forests (RF), or deep learning models such as CNN and RNN. The parameters for each module are trained separately. In this intervention, models, based on the features they extracted, can be categorized into two type: intra-HB feature extraction modules and inter-HB feature extraction modules, and in the case of the extraction module 102, intra-HB features may be extracted As shown in FIG. 1, an attention mechanism is attached to the extraction module 102 and, at S204A, that attention mechanism operates to model dependencies and relationships both between input and output data as well as also between the output data. For instance, by various models with the attachment of an attention mechanism, if an ECG signal was considered to act as a diagnosis for atrial premature complexes, such models and attention mechanism may also show a strong indicator that the same signal would not be a diagnosis for a sinus rhythm at a same time. Additionally, such attention mechanism as applied to the extraction module 102 may also, if a signal shows unchanged pattern among all heartbeats, then show that such signal has high probability to lead to a diagnosis of normal ECG as well as a sinus rhythm. Such dependencies can be modeled as an RNN model, a Bayesian network, etc. and may be used to output illustration or alarm to a user, such as a doctor, technician or researcher, some as framework how to make decisions based on both input and output information.

Figure 3:
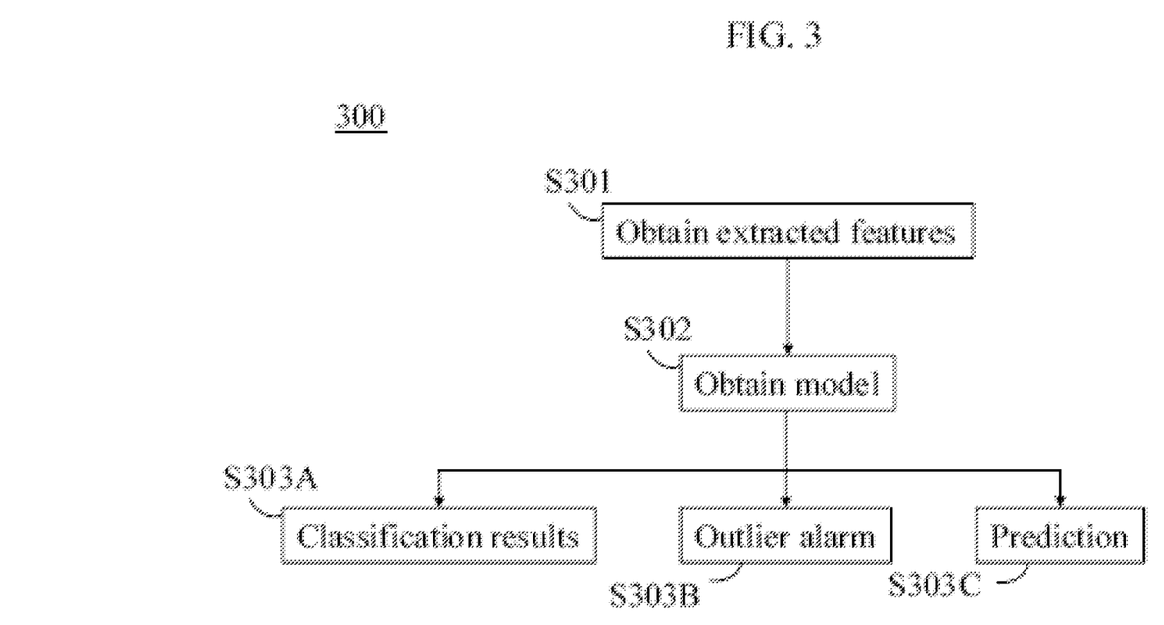
FIG. 3 is a schematic illustration of a simplified flow chart of a communication system in accordance with an embodiment.

At S205A, the process proceeds to post-processing described further with respect to the ECG analysis module 105 and FIG. 3.

At S202B, any of the extraction modules 103 and 104 accept respective ones of pre-processed data as inputs, and generates inter-HB feature vectors as respective outputs.

Model-wise, at S203B, any of the extraction modules 103 and 104 receives one or more models from the extraction module pool 105, and such models include conventional machine learning approaches such as support vector machine (SVM), random forests (RF), or deep learning models such as CNN and RNN as described above.

As shown in FIG. 1, respective attention mechanisms are attached to the extraction modules 103 and 104 and, at S204B, such attention mechanisms operate to model dependencies and relationships both between input and output data as well as also between the output data as described above but with respect to the inter-HB data. Such dependencies from these modules 103 and 104 with their attention mechanisms can also be modeled as an RNN model, a Bayesian network, etc. and may be used to output illustration or alarm to a user, such as a doctor, technician or researcher, some as framework how to make decisions based on both input and output information.

At S205B, the process proceeds to post-processing described further with respect to the ECG analysis module 105 and FIG. 3.

FIG. 3 illustrates a flowchart 300 regarding post processing, and at S301, extracted features, as described with respect to FIG. 2, are collected from multiple of the modules 102, 103 and 104 with multiple types of inputs, and these collected features are post-processed by batch normalization, instance normalization, etc. to provide a final feature set for analysis.

For example, such post-processing involves the ECG analysis module 107 obtaining one or more models from the task specific module pool 105 and S302, and upon obtaining the one or more modules, the ECG analysis module 107 accepts extracted features and produces final outcomes such as any of classification results at S303A, outlier alarms at S304B, and provides predicted diagnosis at S303C for example.

As such, the presently presented training framework is designed as an end-to-end framework that provides a technical solution to the above-described problems in the art. For example, as compared to existing ECG analysis model approaches, the present application may extract features from multiple perspectives simultaneously, such as by the parallel arrangement of the extraction modules 102, 103 and 104 with respect to the reception of ECG signals where such perspectives are, for example, the intra-HB features and inter-HB features described above.

In real-world diagnosis, a doctor or cardiologist needs to consider multi-perspective, heterogeneous and even hierarchical structure features to get a comprehensive conclusion. The present application technically solves such need by merging features from multiple inputs in different forms.

Another advantage is that, the proposed system would help researchers and doctors better understand the correlation among ECG signal and the analysis results such as diagnosis by for example the application of attention to the modules 102, 103 and 104. Moreover, the proposed framework, enhanced technical ease is obtained by to extend the architecture by applying an optional dependence network based on existing cases, such as by the attention add-on for different ones of the extraction modules 102, 103 and 104.

The techniques described above, can be implemented as computer software using computer-readable instructions and physically stored in one or more computer-readable media or by a specifically configured one or more hardware processors. For example, FIG. 4 shows a computer system 400 suitable for implementing certain embodiments of the disclosed subject matter.

The computer software can be coded using any suitable machine code or computer language, that may be subject to assembly, compilation, linking, or like mechanisms to create code comprising instructions that can be executed directly, or through interpretation, micro-code execution, and the like, by computer central processing units (CPUs), Graphics Processing Units (GPUs), and the like.

The instructions can be executed on various types of computers or components thereof, including, for example, personal computers, tablet computers, servers, smartphones, gaming devices, internet of things devices, and the like.

Figure 4:
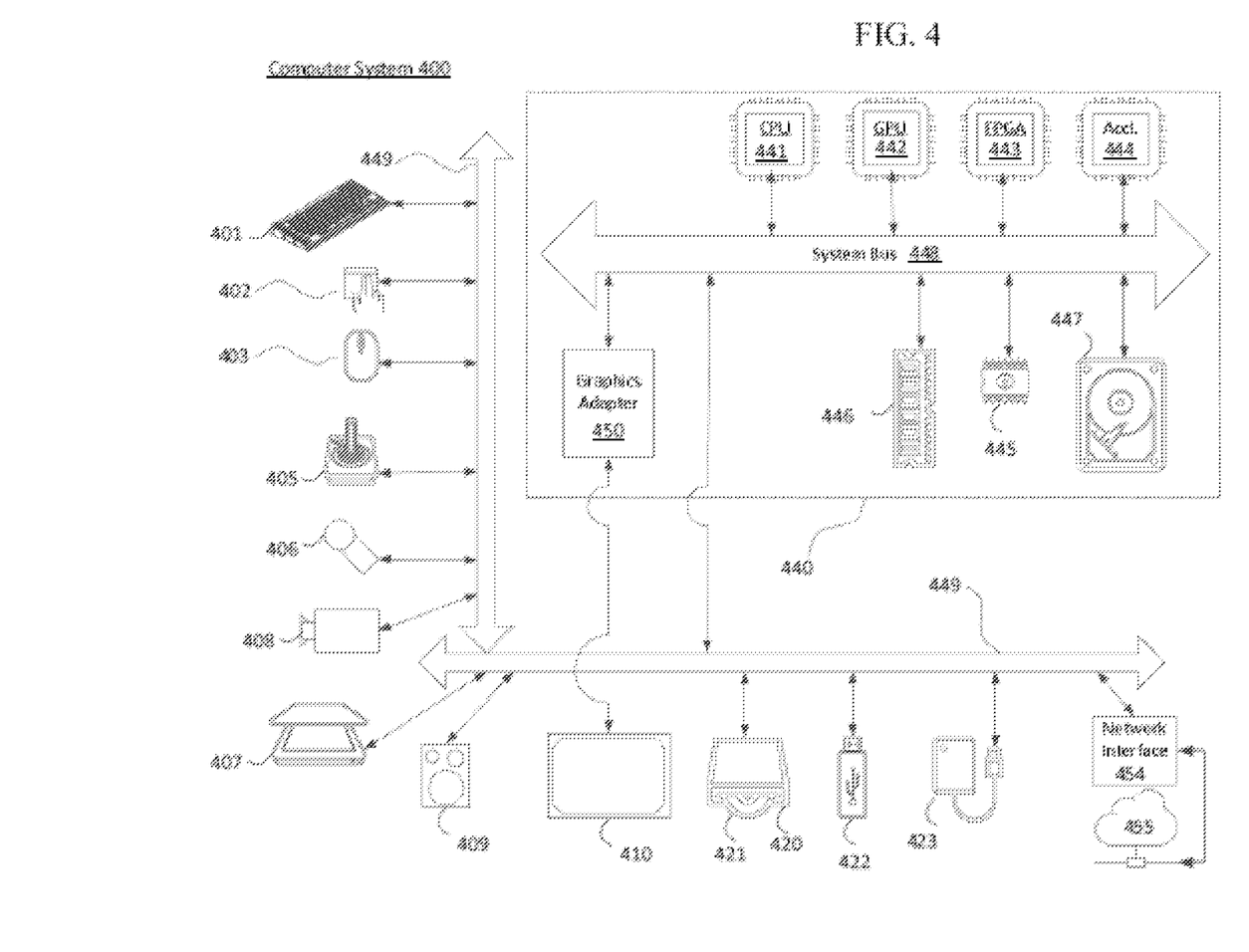
FIG. 4 is a schematic illustration of a simplified block diagram of a system in accordance with an embodiment.

The components shown in FIG. 4 for computer system 400 are exemplary in nature and are not intended to suggest any limitation as to the scope of use or functionality of the computer software implementing embodiments of the present disclosure. Neither should the configuration of components be interpreted as having any dependency or requirement relating to any one or combination of components illustrated in the exemplary embodiment of a computer system 400.

Computer system 400 may include certain human interface input devices. Such a human interface input device may be responsive to input by one or more human users through, for example, tactile input (such as: keystrokes, swipes, data glove movements), audio input (such as: voice, clapping), visual input (such as: gestures), olfactory input (not depicted). The human interface devices can also be used to capture certain media not necessarily directly related to conscious input by a human, such as audio (such as: speech, music, ambient sound), images (such as: scanned images, photographic images obtain from a still image camera), video (such as two-dimensional video, three-dimensional video including stereoscopic video).

Input human interface devices may include one or more of (only one of each depicted): keyboard 401, mouse 402, trackpad 403, touch screen 410, joystick 405, microphone 406, scanner 408, camera 407.

Computer system 400 may also include certain human interface output devices. Such human interface output devices may be stimulating the senses of one or more human users through, for example, tactile output, sound, light, and smell/taste. Such human interface output devices may include tactile output devices (for example tactile feedback by the touch-screen 410, or joystick 405, but there can also be tactile feedback devices that do not serve as input devices), audio output devices (such as: speakers 409, headphones (not depicted)), visual output devices (such as screens 410 to include CRT screens, LCD screens, plasma screens, OLED screens, each with or without touch-screen input capability, each with or without tactile feedback capability—some of which may be capable to output two dimensional visual output or more than three dimensional output through means such as stereographic output; virtual-reality glasses (not depicted), holographic displays and smoke tanks (not depicted)), and printers (not depicted).

Computer system 400 can also include human accessible storage devices and their associated media such as optical media including CD/DVD ROM/RW 420 with CD/DVD or the like media 421, thumb-drive 422, removable hard drive or solid state drive 423, legacy magnetic media such as tape and floppy disc (not depicted), specialized ROM/ASIC/PLD based devices such as security dongles (not depicted), and the like.

Those skilled in the art should also understand that term "computer readable media" as used in connection with the presently disclosed subject matter does not encompass transmission media, carrier waves, or other transitory signals.

Computer system 400 can also include interface to one or more communication networks. Networks can for example be wireless, wireline, optical. Networks can further be local, wide-area, metropolitan, vehicular and industrial, real-time, delay-tolerant, and so on. Examples of networks include local area networks such as Ethernet, wireless LANs, cellular networks to include GSM, 3G, 4G, 5G, LTE and the like, TV wireline or wireless wide area digital networks to include cable TV, satellite TV, and terrestrial broadcast TV, vehicular and industrial to include CANBus, and so forth. Certain networks commonly require external network interface adapters that attached to certain general-purpose data ports or peripheral buses (449) (such as, for example USB ports of the computer system 400; others are commonly integrated into the core of the computer system 400 by attachment to a system bus as described below (for example Ethernet interface into a PC computer system or cellular network interface into a smartphone computer system). Using any of these networks, computer system 400 can communicate with other entities. Such communication can be uni-directional, receive only (for example, broadcast TV), uni-directional send-only (for example CANbusto certain CANbus devices), or bi-directional, for example to other computer systems using local or wide area digital networks. Certain protocols and protocol stacks can be used on each of those networks and network interfaces as described above.

Aforementioned human interface devices, human-accessible storage devices, and network interfaces can be attached to a core 440 of the computer system 400.

The core 440 can include one or more Central Processing Units (CPU) 441, Graphics Processing Units (GPU) 442, specialized programmable processing units in the form of Field Programmable Gate Areas (FPGA) 443, hardware accelerators for certain tasks 444, and so forth. These devices, along with Read-only memory (ROM) 445, Random-access memory 446, internal mass storage such as internal non-user accessible hard drives, SSDs, and the like 447, may be connected through a system bus 448. In some computer systems, the system bus 448 can be accessible in the form of one or more physical plugs to enable extensions by additional CPUs, GPU, and the like. The peripheral devices can be attached either directly to the core's system bus 448, or through a peripheral bus 449. Architectures for a peripheral bus include PCI, USB, and the like.

CPUs 441, GPUs 442, FPGAs 443, and accelerators 444 can execute certain instructions that, in combination, can make up the aforementioned computer code. That computer code can be stored in ROM 445 or RAM 446. Transitional data can be also be stored in RAM 446, whereas permanent data can be stored for example, in the internal mass storage 447. Fast storage and retrieve to any of the memory devices can be enabled through the use of cache memory, that can be closely associated with one or more CPU 441, GPU 442, mass storage 447, ROM 445, RAM 446, and the like.

The computer readable media can have computer code thereon for performing various computer-implemented operations. The media and computer code can be those specially designed and constructed for the purposes of the present disclosure, or they can be of the kind well known and available to those having skill in the computer software arts.

As an example and not by way of limitation, the computer system having architecture 400, and specifically the core 440 can provide functionality as a result of processor(s) (including CPUs, GPUs, FPGA, accelerators, and the like) executing software embodied in one or more tangible, computer-readable media. Such computer-readable media can be media associated with user-accessible mass storage as introduced above, as well as certain storage of the core 440 that are of non-transitory nature, such as core-internal mass storage 447 or ROM 445. The software implementing various embodiments of the present disclosure can be stored in such devices and executed by core 440. A computer-readable medium can include one or more memory devices or chips, according to particular needs. The software can cause the core 440 and specifically the processors therein (including CPU, GPU, FPGA, and the like) to execute particular processes or particular parts of particular processes described herein, including defining data structures stored in RAM 446 and modifying such data structures according to the processes defined by the software. In addition or as an alternative, the computer system can provide functionality as a result of logic hardwired or otherwise embodied in a circuit (for example: accelerator 444), which can operate in place of or together with software to execute particular processes or particular parts of particular processes described herein. Reference to software can encompass logic, and vice versa, where appropriate. Reference to a computer-readable media can encompass a circuit (such as an integrated circuit (IC)) storing software for execution, a circuit embodying logic for execution, or both, where appropriate. The present disclosure encompasses any suitable combination of hardware and software.

Besides the mentioned design and procedure of the proposed framework, there are several alternatives:

The extraction module may use a combination of several algorithms and structures, for instance, RNN with CNN, RNN with a support vector machine (SVM), etc. Since the flexibility of definition of "feature" in machine learning, the exact implementation of extraction modules may vary as would be recognized from this application.

Further, the perspectives of feature extraction are flexible and although there is described use of intra-HB and inter-HB categories above, alternatives, may use: HB, QRS wave, T wave, etc. as hierarchical categories for feature extraction.

Moreover, the attention add-on are also flexible in that the attention may or may not be used for certain modules and also that a same or different attentions may be applied to different modules depending on the requirement and purpose of feature extraction.

For feature extraction modules, similar models could share a subset of parameters to account the similarity among inputs.

Presently, the framework is designed as an end-to-end procedure that the whole framework will be optimized and altered simultaneously according to exemplary embodiments, and an alternative may be a step-by-step training procedure, in which the extraction modules can be trained separately, for instance, using encoder and decoder structure, according to other embodiments.

This approach can be extended to other applications which have multiple sources of inputs.

Figure 5:
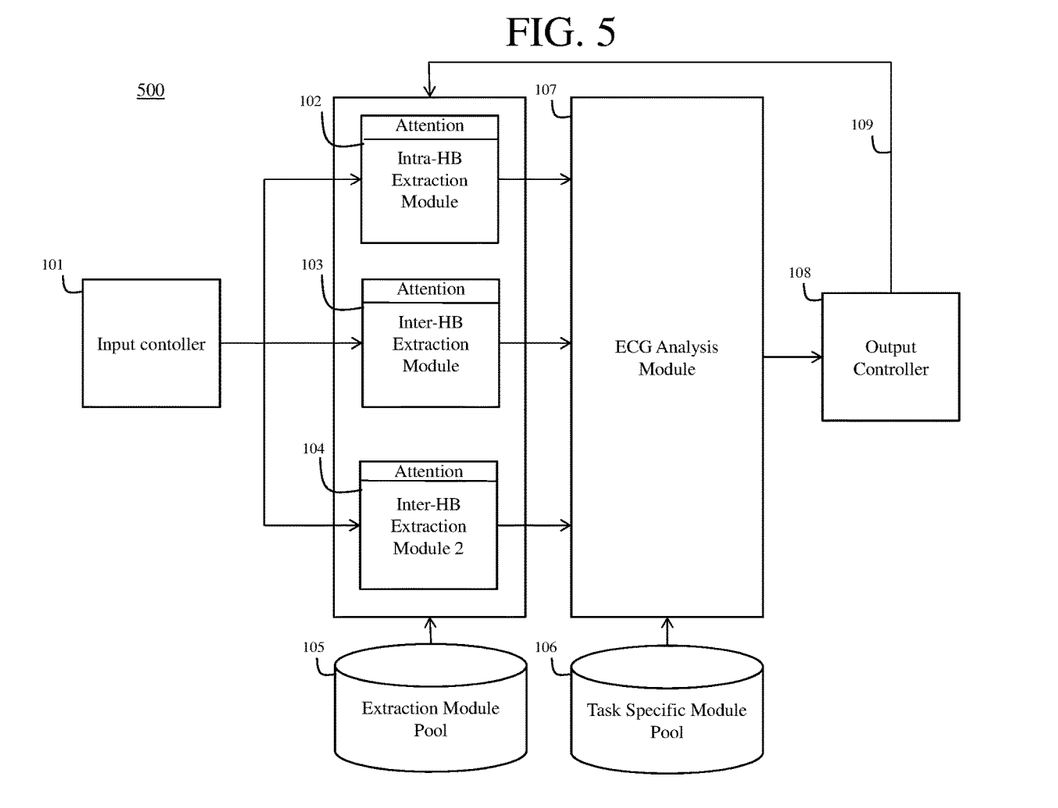
FIG. 5 is a schematic illustration of a simplified flow chart of a communication system in accordance with an embodiment.

Further, there may be, based on the extraction modules and analysis tasks selected to apply with, optional feedback mechanisms added from an output to the feature extraction modules 102, 103 and 104. For instance, in an RNN model for multi-symptom diagnosis, according to exemplary embodiments, such feedback mechanisms may further account for dependencies among symptoms, and a feedback link 109, as shown in the system 500 of FIG. 5, can be added from diagnosed symptoms to feature extraction modules 102, 103 and 104, in to inform one or more of the extraction modules 102, 103 and 104 and one or more of their attention mechanisms how and where to concentrate or focus in subsequent steps.

While this disclosure has described several exemplary embodiments, there are alterations, permutations, and various substitute equivalents, which fall within the scope of the disclosure. It will thus be appreciated that those skilled in the art will be able to devise numerous systems and methods which, although not explicitly shown or described herein, embody the principles of the disclosure and are thus within the spirit and scope thereof.

What is claimed is:

1. An apparatus comprising:
   at least one memory configured to store computer program code;
   at least one hardware processor configured to access said computer program code and operate as instructed by said computer program code, said computer program code including:
   intra-heartbeat (HB) extraction code configured to cause the at least one hardware processor to extract intra-HB features from electrocardiography (ECG) signals;
   inter-HB extraction code configured to cause the at least one hardware processor to extract inter-HB features from the ECG signals;
   attention mechanism code configured to cause the at least one hardware processor to control the extraction of the inter-HB and intra-HB features based on at least one attention mechanism; and
   ECG analysis code configured to cause the at least one hardware processor to obtain and statistically process the intra-HB features and the inter-HB features,
   wherein the ECG analysis code is further configured to cause the at least one hardware processor to output at least an outlier alarm based on a result of statistically processing the intra-HB features and the inter-HB features, and
   wherein the intra-HB extraction code is further configured to cause the at least one hardware processor to extract the intra-HB features in parallel with extraction of the inter-HB features.

2. The apparatus according to claim 1, wherein the computer program code further includes extraction pool code configured to cause the at least one hardware processor to extract at least one extraction model from an extraction pool and apply the at least one extraction model to extraction of at least one of the intra-HB features and the inter-HB features by a corresponding one of the intra-HB extraction code and the inter-HB extraction code.

3. The apparatus according to claim 1, wherein the computer program code further includes second inter-HB extraction code configured to cause the at least one processor to extract second inter-HB features from the ECG signals in parallel with both of the extraction of the intra-HB features and the extraction of the inter-HB features.

4. The apparatus according to claim 3, wherein the at least one attention mechanism code is configured to cause the at least one hardware processor to control the intra-HB extraction based on the at least one attention mechanism, and
   wherein the computer program code further includes:
   second attention mechanism code configured to cause the at least one hardware processor to control the inter-HB extraction based on a second attention mechanism; and
   third attention mechanism code configured to cause the at least one hardware processor to control the second inter-HB extraction based on a third attention mechanism.

5. The apparatus according to claim 1, wherein the computer program code further includes task specific pool code configured to cause the at least one hardware processor to extract at least one task specific model from a task specific pool and apply the at least one task specific model to statistically process the intra-HB features and the inter-HB features.

6. The apparatus according to claim 5, wherein the ECG analysis code is further configured to cause the at least one hardware processor to output further at least one of a classification result and a predicted diagnosis based on the result of statistically processing the intra-HB features and the inter-HB features.

7. The apparatus according to claim 6, wherein statistically processing the intra-HB features and the inter-HB features comprises at least one of batch normalization and instance normalization based on the at least one task specific model.

8. The apparatus according to claim 7, wherein computer program code further includes feedback link code configured to cause the at least one hardware processor to feedback an output of the ECG analysis code to the at least one attention mechanism, and
   wherein the at least one attention mechanism code is configured to cause the at least one hardware processor to update the attention mechanism based on the output.

9. A method performed by at least one computer processor comprising:
   extracting intra-HB features from electrocardiography (ECG) signals;
   extracting, inter-HB features from the ECG signals;
   controlling at least one of the intra-HB extraction and inter-HB extraction based on at least one attention mechanism;
   obtaining and statistically processing the intra-HB features and the inter-HB features; and outputting at least an outlier alarm based on a result of statistically processing the intra-HB features and the inter-HB features,
wherein extracting the intra-HB features is in parallel with extraction of the inter-HB features.

10. The method according to claim 9, further comprising:
extracting at least one extraction model from an extraction pool and applying the at least one extraction model to extraction of at least one of the intra-HB features and the inter-HB features.

11. The method according to claim 9, further comprising:
extracting second inter-HB features from the ECG signals in parallel with both of the extraction of the intra-HB features and the extraction of the inter-HB.

12. The method according to claim 11, further comprising:
controlling the intra-HB extraction based on the at least one attention mechanism;
controlling the inter-HB extraction based a second attention mechanism; and
controlling the second inter-HB extraction based on a third attention mechanism.

13. The method according to claim 9, further comprising:
extracting at least one task specific model from a task specific pool; and
applying the at least one task specific model to statistically process the intra-HB features and the inter-HB features.

14. The method according to claim 13, further comprising:
outputting at least one of a classification result and a predicted diagnosis based on the result of statistically processing the intra-HB features and the inter-HB features.

15. The method according to claim 14, wherein statistically processing the intra-HB features and the inter-HB features comprises at least one of batch normalization and instance normalization based on the at least one task specific model.

16. A non-transitory computer readable medium storing a program causing a computer to execute a process, the process comprising:
extracting intra-HB features from electrocardiography (ECG) signals;
extracting inter-HB features from the ECG signals;
controlling at least one of the intra-HB extraction and inter-HB extraction based on at least one attention mechanism;
obtaining and statistically processing the intra-HB features and the inter-HB features; and
outputting at least an outlier alarm based on a result of statistically processing the intra-HB features and the inter-HB features,
wherein extracting the intra-HB features is in parallel with extraction of the inter-HB features.

* * * * *